United States Patent
Wang et al.

(10) Patent No.: US 9,752,972 B2
(45) Date of Patent: Sep. 5, 2017

(54) TRANSISTOR-TYPE VISCOSITY SENSOR, AND VISCOSITY MEASUREMENT SYSTEM AND VISCOSITY MEASURING METHOD USING THE SAME

(71) Applicant: National Tsing Hua university, Hsinchu (TW)

(72) Inventors: Yu-Lin Wang, Hsinchu (TW); Jen-Inn Chyi, Hsinchu (TW); Jung-Ying Fang, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 455 days.

(21) Appl. No.: 14/298,999

(22) Filed: Jun. 9, 2014

(65) Prior Publication Data
US 2015/0255546 A1   Sep. 10, 2015

(30) Foreign Application Priority Data
Mar. 7, 2014  (TW) .............................. 103107982 A

(51) Int. Cl.
G01N 11/02  (2006.01)
G01N 11/00  (2006.01)

(52) U.S. Cl.
CPC ............. *G01N 11/02* (2013.01); *G01N 11/00* (2013.01); *G01N 2011/0066* (2013.01)

(58) Field of Classification Search
CPC . G01N 11/00; G01N 11/02; G01N 2011/0066
USPC ....................................................... 73/54.01
See application file for complete search history.

(56) References Cited

U.S. PATENT DOCUMENTS

| | | | |
|---|---|---|---|
| 2002/0066908 A1* | 6/2002 | Smith ............... | H01L 29/42316 257/194 |
| 2011/0137184 A1 | 6/2011 | Ren et al. | |
| 2013/0204107 A1 | 8/2013 | Lee et al. | |

OTHER PUBLICATIONS

Non-Patent Literature "Boron trifluoride", accessed at http://web.archive.org/web/20120403023914/Boron_trifluoride, archived on Apr. 3, 2012.*

(Continued)

*Primary Examiner* — Daniel S Larkin
*Assistant Examiner* — Irving A Campbell
(74) *Attorney, Agent, or Firm* — Li & Cai Intellectual Property (USA) Office

(57) ABSTRACT

A viscosity measurement system, which is for measuring the viscosity of a fluid, comprises a transistor-type viscosity sensor, an electrical measurement unit, and a processing unit. The transistor-type viscosity sensor includes a semiconductor structure, a source terminal, and a drain terminal. The semiconductor structure includes a GaN layer and an AlGaN layer disposed on the GaN layer. The portion of the semiconductor structure that is between the source terminal and the drain terminal has a gate region, which has an exposed surface for being in contact with the fluid. The electrical measurement unit is in electrical connection with the source terminal and the drain terminal and for measuring an electronic signal of the semiconductor structure. The processing unit is coupled to the electrical measurement unit and for determining the viscosity of the fluid according to the electronic signal measured.

30 Claims, 7 Drawing Sheets

(56) References Cited

OTHER PUBLICATIONS

Non Patent Literature "Solvent", accessed at http://web.archive.org/web/20130120185015/http://en.wikipedia.org/wiki/Solvent, archived on Jan. 20, 2013.*

Khanna, Vinod Kumar, Robust HEMT Microsensors as Prospective Successors of MOSFET/ISFET Detectors in Harsh Environments, Frontiers in Sensors (FS) vol. 1 Issue 3, Jul. 2013.*

Edwards, M.J. et al., Pressure and temperature dependence of GaN/AlGaN high electron mobility transistor based sensors on a sapphire membrane, Phys. Status Solidi C 9, No. 3-4, 960-963 (2012).*

Hydrogen chloride, accessed at http://web.archive.org/web/20130305212545/http://en.wikipedia.org/wiki/Hydrogen_chloride, archived on Mar. 5, 2013.*

\* cited by examiner

TRANSISTOR-TYPE VISCOSITY SENSOR, AND VISCOSITY MEASUREMENT SYSTEM AND VISCOSITY MEASURING METHOD USING THE SAME

BACKGROUND

1. Field of the Invention

The instant disclosure relates to measurement system and measuring method, and pertains particularly to a viscosity measurement system having transistor-type viscosity sensor and viscosity measuring method.

2. Description of Related Art

When applied to a limited amount of fluid to be measured, existing viscosity sensor system and viscosity measuring method are still limited to the error caused by the small amount of fluids.

The HEMTs (high electron mobility transistors) have been demonstrated for gas, chemical, and bio-sensing applications. In using the HEMTs as sensors, the signal to noise ratio attracts great interest. While much research has focused on how to increase the signal for sensors, it is crucial to realize how the noise resulted. Since the drain current or the conductivity at a fixed bias voltage of the HEMT-bases sensor are usually monitored, it is now known that the drift and the fluctuation of the baseline current are common sources of noise for sensors.

SUMMARY OF THE INVENTION

The embodiment of the instant disclosure provides a viscosity measurement system and a viscosity measuring method. The viscosity measurement system utilizes an exposed gate region as a contact window for measuring the viscosity of a fluid.

The viscosity measurement system in accordance with the instant disclosure comprises a transistor-type viscosity sensor, an electrical measurement unit, and a processing unit. The transistor-type viscosity sensor includes a semiconductor structure, a source terminal, and a drain terminal. The semiconductor structure includes a GaN layer and an AlGaN layer disposed on the GaN layer. The source terminal and the drain terminal respectively are in ohmic contact with the AlGaN layer. The portion of the semiconductor structure that is between the source terminal and the drain terminal has a gate region, which has an exposed surface for being in contact with the fluid. The electrical measurement unit is in electrical connection with the source terminal and the drain terminal and for measuring an electronic signal of the semiconductor structure. The processing unit is coupled to the electrical measurement unit and for determining the viscosity of the fluid according to the electronic signal measured by the electrical measurement unit.

Another aspect of the instant disclosure provides a viscosity measuring method for measuring the viscosity of a fluid, which comprises the following steps. First, a transistor-type viscosity sensor, which includes a semiconductor structure, a source terminal, and a drain terminal, is provided. The semiconductor structure includes a GaN layer and an AlGaN layer disposed on the GaN layer. The source terminal and the drain terminal respectively are in ohmic contact with the AlGaN layer. The portion of the semiconductor structure that is between the source terminal and the drain terminal has a gate region, and the gate region has an exposed surface. The fluid is then put into contact with the exposed surface of the gate region. And then, an electronic signal of the semiconductor structure is measured. The viscosity of the fluid is then determined according to the electronic signal measured by the electrical measurement unit.

In accordance with an embodiment, the present disclosure provides a viscosity measurement system and a viscosity measuring method, which utilize the semiconductor structure including a GaN layer and an AlGaN layer serving as a high electron mobility transistor, and utilize the gate region open to the fluid sample, serving as the contact window for sensing, to allow the fluid to cross the exposed surface of the gate region, whereby measuring the viscosity of the fluid through measuring electronic signal of the semiconductor structure.

These and other features and advantages of the present invention will be described in, or will become apparent to those of ordinary skill in the art in view of, the following detailed description of the exemplary embodiments of the present invention.

BRIEF DESCRIPTION OF THE DRAWINGS

The novel features believed characteristic of the invention are set forth in the appended claims. The invention itself, however, as well as a preferred mode of use, further objectives and advantages thereof, will best be understood by reference to the following detailed description of an illustrative embodiments when read in conjunction with the accompanying drawings, wherein:

DETAILED DESCRIPTION OF THE PREFERRED EMBODIMENTS

The instant disclosure will be described more specifically with reference to the following embodiments. It is to be noted that the following descriptions of preferred embodiments are provided herein for purpose of illustration and description. It is not intended to be exhaustive or limiting to the precise form disclosed.

Figure 1:
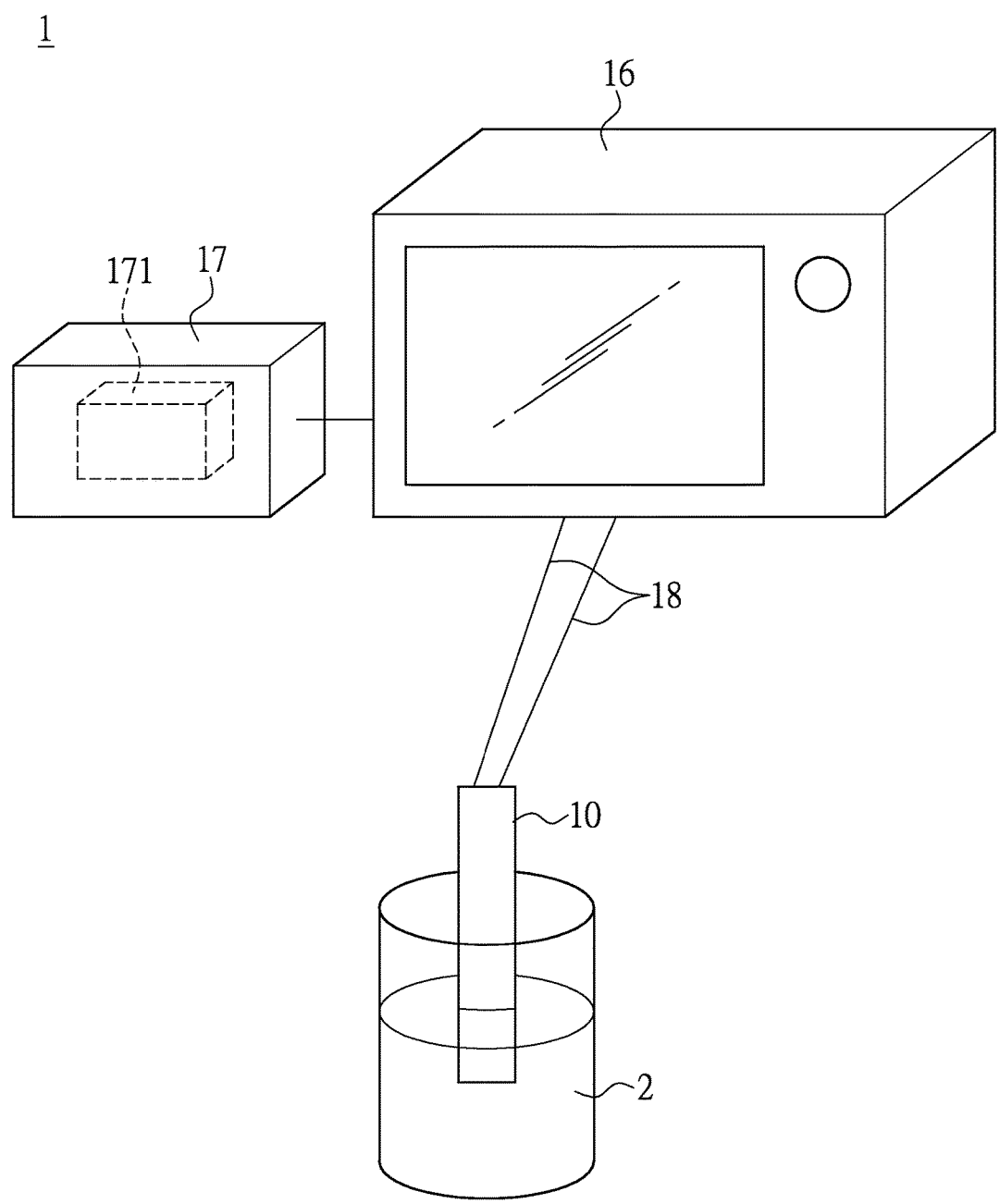
FIG. 1 illustrates a schematic view of a viscosity measurement system in accordance with an embodiment of the present disclosure.
Figure 2:
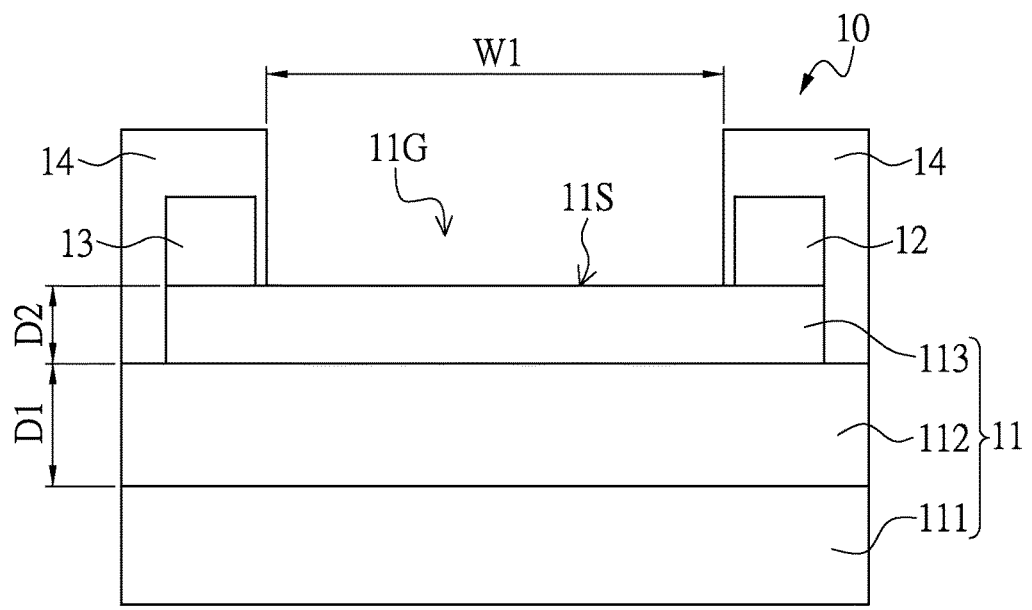
FIG. 2 illustrates a partial cross-section view of a transistor-type viscosity sensor in accordance with an embodiment of the present disclosure.
Figure 3:
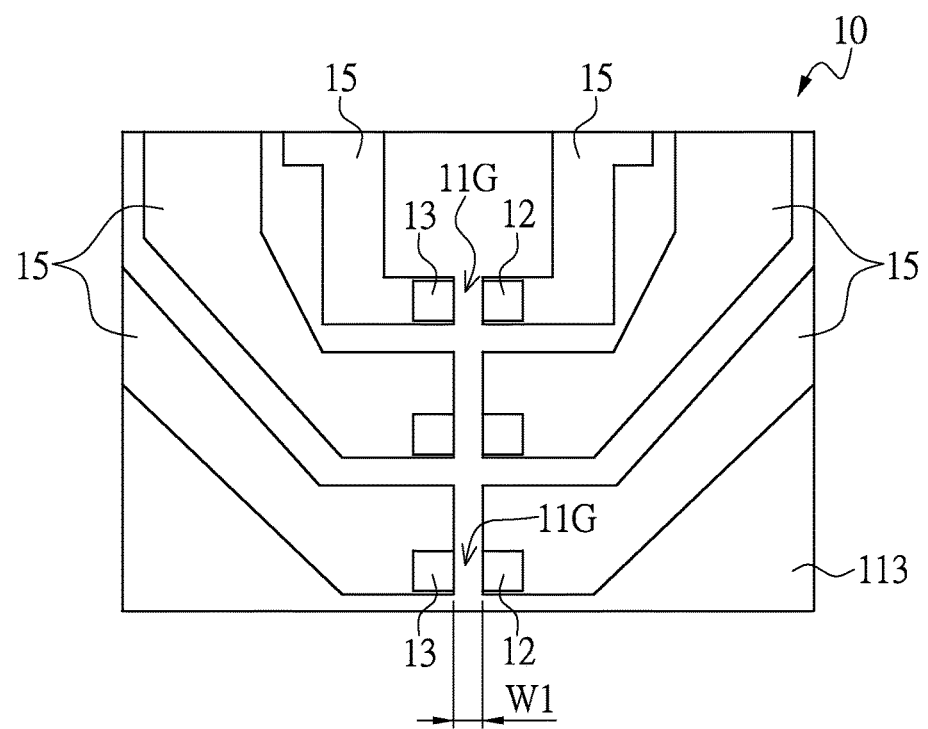
FIG. 3 illustrates a regional plan view of the transistor-type viscosity sensor without passivation layer in accordance with an embodiment of the present disclosure.

Please refer concurrently to FIG. 1, FIG. 2, and FIG. 3. FIG. 1 illustrates a schematic view of a viscosity measurement system in accordance with an embodiment of the present disclosure. FIG. 2 illustrates a partial cross-section view of a transistor-type viscosity sensor in accordance with an embodiment of the present disclosure. FIG. 3 illustrates a regional plan view of the transistor-type viscosity sensor without passivation layer in accordance with an embodiment of the present disclosure.

The viscosity measurement system 1 is adapted for measuring the viscosity of a fluid 2 and comprises a transistor-type viscosity sensor 10, an electrical measurement unit 16, and a processing unit 17. As shown in FIG. 2 and FIG. 3, the transistor-type viscosity sensor 10 includes a semiconductor structure 11, a source terminal 12, and a drain terminal 13, where the source terminal 12 and the drain terminal 13 each are in ohmic contact with the semiconductor structure 11, which may serve as a conducting channel between the source terminal 12 and the drain terminal 13. In the instant disclosure, the transistor-type viscosity sensor 10 further includes a wiring layer 15 and a passivation layer 14, where the wiring layer 15 is in electrical connection with the source terminal 12 and the drain terminal 13 respectively and the passivation layer 14 is covering both the source terminal 12 and the drain terminal 13. The following describes the features of the components of the transistor-type viscosity sensor 10 in detail.

The semiconductor structure 11 includes a substrate 111, a GaN (gallium nitride) layer 112 disposed on the substrate 111, and an AlGaN (aluminium gallium nitride) layer 113 disposed on the GaN layer 112. In the instant disclosure, the semiconductor structure 11 can be formed of an epitaxy wafer structure, the GaN layer 112 can be an undoped GaN buffer having a thickness D1 of, as a specific example, 3 micrometers.

The AlGaN layer 113 is for inducing high spontaneous polarization, which generated a two-dimensional electron gas beneath the AlGaN layer 113. The AlGaN layer 113 can be an undoped AlGaN layer having a thickness D2 of, as a specific example, 13.5 to 16.5 nanometers. The AlGaN layer 113 may include an aluminium gallium nitride material that has the molecular formula of $Al_{0.25}Ga_{0.75}N$. In an alternative embodiment, the mole percent of aluminium in the AlGaN layer 113 may range from 22% to 28%. In a preferred embodiment, the thickness D2 of the AlGaN layer 113 is about 15 nanometers, and the mole percent of aluminium in the AlGaN layer 113 is about 25%. In addition, in other embodiments not shown in the Figures, the semiconductor structure 11 may further comprise a GaN cap layer, which can be formed of, for example, an undoped GaN layer having a thickness of 10 angstroms.

These epilayers (e.g. the GaN layer 112 and the AlGaN layer 113) can be grown by metal-organic chemical vapor deposition (MOCVD) on the substrate 111, such as a sapphire substrate. The substrate 111 may have an array of active areas (not shown in the Figures). Specifically, through an etching process, the epilayers 112, and 113 can be formed with a pattern to expose the substrate 111, thereby defining at least one of the active areas. For example, the pattern may comprise a plurality of recesses, and the etching process can be a mesa isolation process. To put it concretely, the mesa isolation can be performed using an Inductively Coupled Plasma (ICP) etching system with $Cl_2/BCl_3$ gases under ICP power of 300 W at 2 MHz and a process pressure of 10 mTorrs.

The source terminal 12 and the drain terminal 13 each are in ohmic contact with the AlGaN layer 113. Moreover, the portion of the semiconductor structure 11 that is between the source terminal 12 and the drain terminal 13 has a gate region 11G. In the instant disclosure, the source terminal 12 and the drain terminal 13 can be disposed at the respective lateral sides of the gate region 11G. It is worth mentioned that, the gate region 11G has an exposed surface 11S for being in contact with the fluid 2 to be measured.

As a specific example, the ohmic contacts of the source terminal 12 and the drain terminal 13 each have a area of 60×60 $\mu m^2$, and the width W1 of the exposed surface 11S of the gate region 11G ranges from 27 to 33 micrometers. In a preferred embodiment, the width W1 of the exposed surface 11S of the gate region 11G is about 30 micrometers. The source terminal 12 and the drain terminal 13 can each be formed by an e-beam deposition and then annealed at 850° C., 45 seconds under flowing $N_2$. The source terminal 12 and the drain terminal 13 may comprise an ohmic-contact conductive material including at least one selected from titanium, aluminum, nickel, and gold. In an alternatively embodiment, the semiconductor structure 11 may further includes a gold layer disposed on the portion of the AlGaN layer that comprises the gate region, the thickness of the gold layer can be about 100 angstroms.

The wiring layer 15 is disposed on the semiconductor structure 11 and comprises a conductive material such as titanium and gold. The wiring layer 15 is patterned, and the pattern thereof can be modified according to need and realized by those skilled in the art and the instant disclosure is not limited to the pattern of the wiring layer 15 shown in FIG. 3.

The passivation layer 14 is covering most of the surface of transistor-type viscosity sensor 10 except for the exposed surface 11S of the gate region 11G, as to encapsulate the source terminal 12 and the drain terminal 13 with only the gate region 11G open, whereby allowing the fluid 2 to be in direct contact with the exposed surface 11S. As a specific example, the passivation layer 14 comprises a photoresist material (e.g. photoresist material Shipley S1818) and has a thickness of about 1.8 micrometers.

As shown in FIG. 1, the electrical measurement unit 16 is in electrical connection with the source terminal 12 and the drain terminal 13, for measuring an electronic signal of the semiconductor structure 11. In the instant disclosure, the electrical measurement unit 16 is for measuring a current fluctuation of the semiconductor structure 11 at a determined drain-source bias. In an exemplary embodiment, the electrical measurement unit 16 can be a Agilent B1500 Semiconductor Device Parameter Analyzer from Agilent Technology in Santa Clara, Calif. USA, and is electrically connected to the wiring layer 15 via wires 18 for applying a determined bias and measuring a base line current of the semiconductor structure 11 at a determined drain-source bias. The electrical measurement unit 16 can further be used to record the data of the base line current of the semiconductor structure 11 from a real-time measurement for monitoring the current fluctuation of the semiconductor structure 11, which is, for example, defined by standard deviation from the real-time measurement of the drain current.

Figure 4:
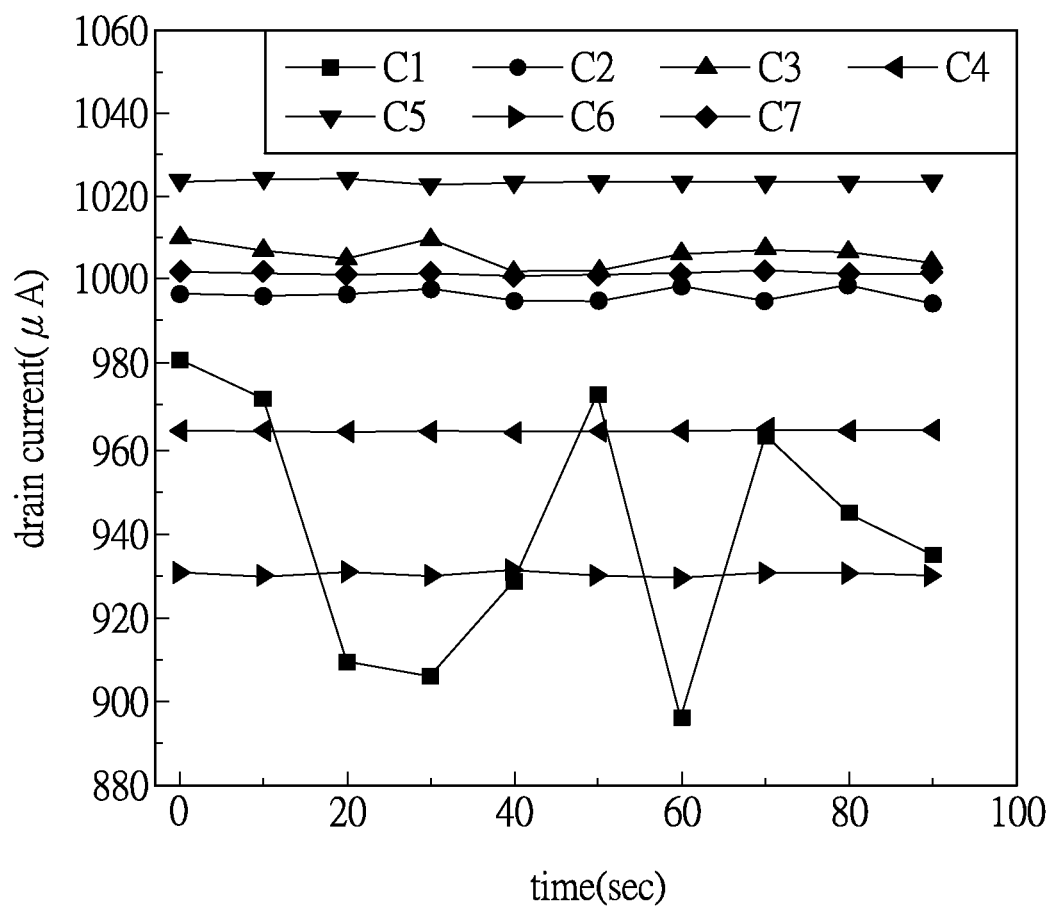
FIG. 4 illustrates the real time measurements of the drain current for the transistor-type viscosity sensor in accordance with an embodiment of the present disclosure.

Please refer to FIG. 4, which illustrates the real time measurements of the drain current for the transistor-type viscosity sensor in accordance with an embodiment of the present disclosure. In FIG. 4, the horizontal axis represents the time in the unit of second, and the vertical axis represents the amount of the current measured in the unit of microampere ($\mu A$). The result shown in FIG. 4 is abstained under the condition of: submerging the transistor-type viscosity sensor 10 in the fluids 2 to be measured, such as deionized water, dimethyl sulfoxide (DMSO), ethanol, air, glycerol, ethylene glycol, and 1, 2-butandiol respectively at room temperature, and applying a source-drain bias of 0.5 volts through the electrical measurement unit 16, where the interval time between any two measurement points is set as 10 seconds and the temperature is kept at room temperature for all the fluids 2.

As shown in FIG. 4, the curve C1 shows the real-time measurement of the drain current of the semiconductor structure 11 for deionized water. The curve C2 shows the real-time measurement of the drain current of the semiconductor structure 11 for dimethyl sulfoxide (DMSO). The curve C3 shows the real-time measurement of the drain current of the semiconductor structure 11 for ethanol. The curve C4 shows the real-time measurement of the drain current of the semiconductor structure 11 for air. The curve C5 shows the real-time measurement of the drain current of the semiconductor structure 11 for glycerol. The curve C6 shows the real-time measurement of the drain current of the semiconductor structure 11 for ethylene glycol. The curve C7 shows the real-time measurement of the drain current of the semiconductor structure 11 for 1, 2-butandiol.

The processing unit 17, which is coupled to the electrical measurement unit 16, is for determining the viscosity of the fluid 2 according to the electronic signal measured by the electrical measurement unit 16. In the instant embodiment, the processing unit 17 includes a data storage module 171 for storing a look-up datum. The content of the look-up datum includes the relationship between the viscosity of fluid and the current fluctuation of the semiconductor structure 11 at a determined drain-source bias. The processing unit 17 of the instant embodiment is for determining the viscosity of the fluid 2 according to the current fluctuation measured by the electrical measurement unit 16 and based on the look-up datum.

Figure 5A:
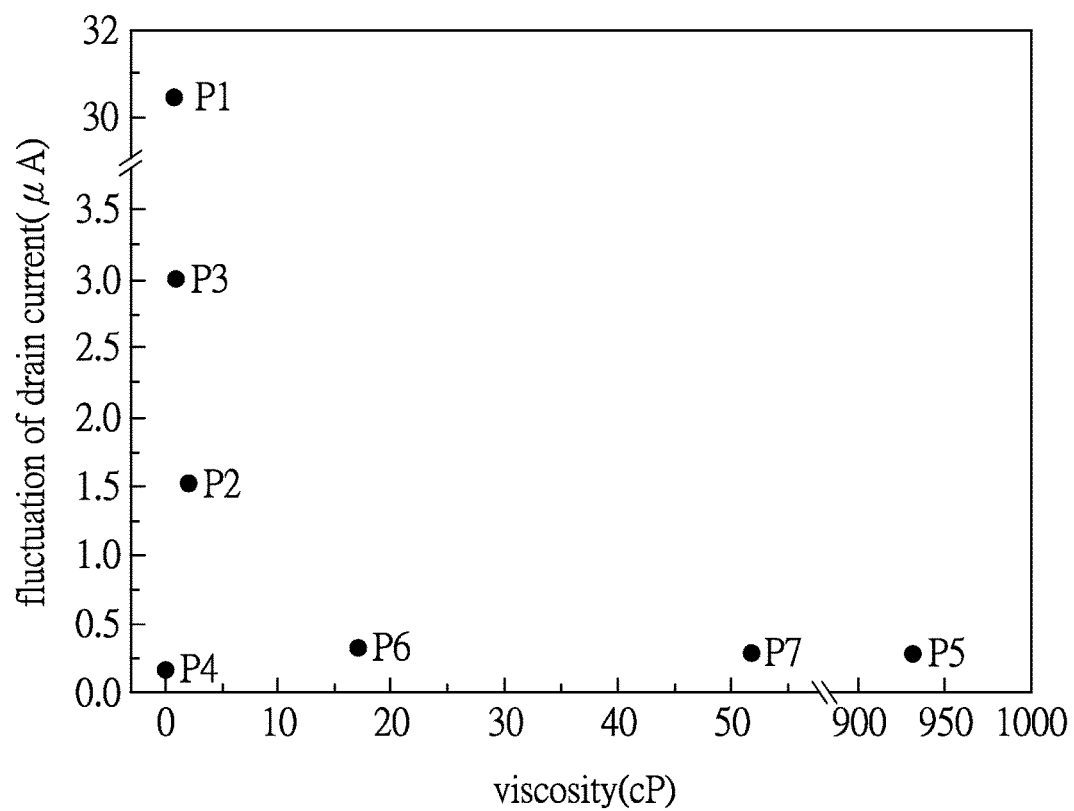
FIG. 5A, FIG. 5B, and FIG. 5C show the fluctuation of drain current of the transistor-type viscosity sensor versus the viscosity for various liquids in accordance with an embodiment of the present disclosure.
Figure 5B:
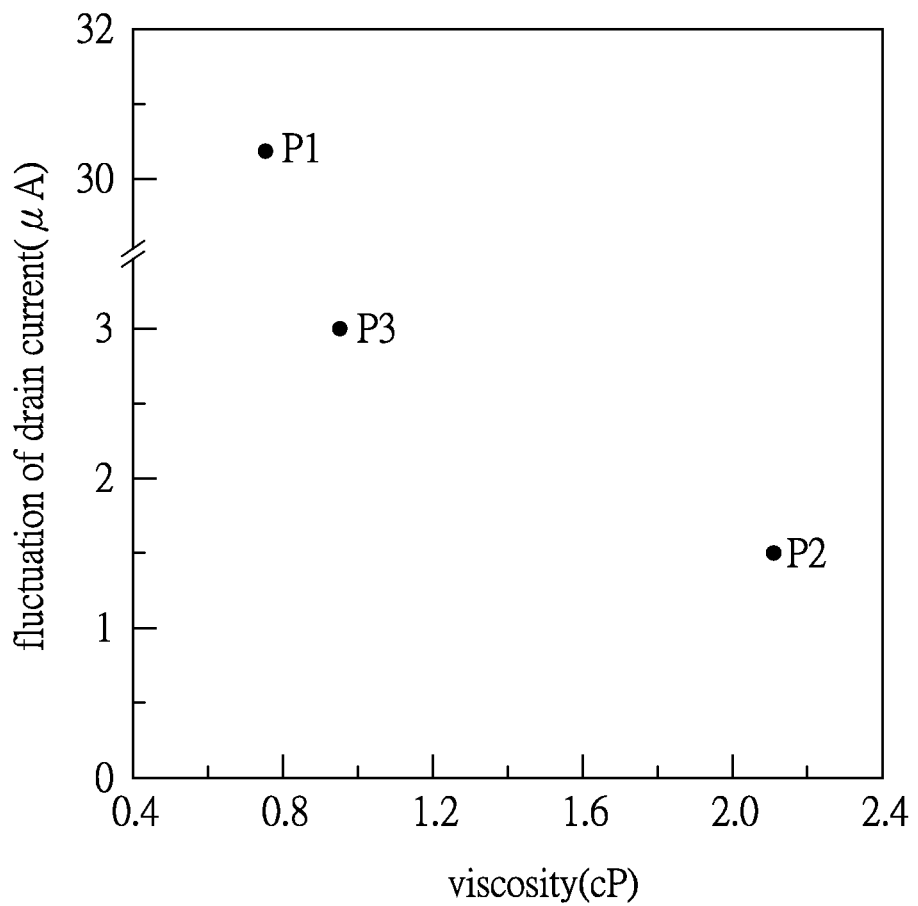
Figure 5C:
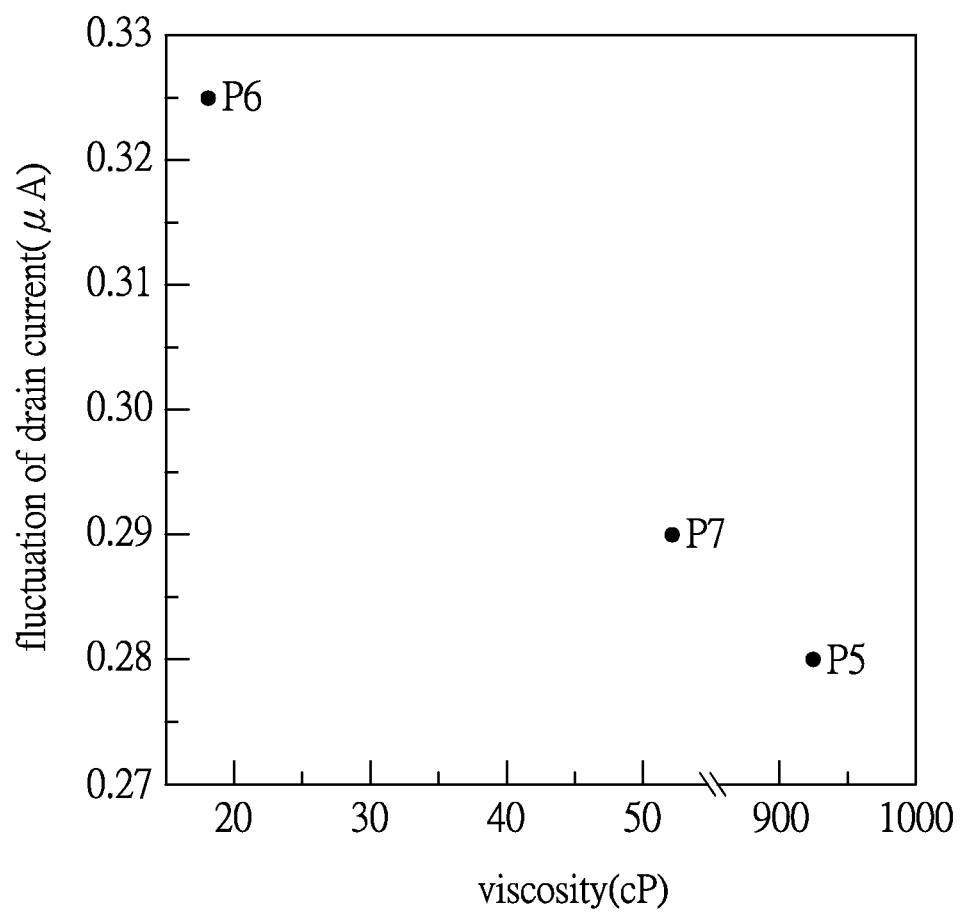

Please refer to FIG. 5A, FIG. 5B, and FIG. 5C, which show the fluctuation of drain current of the transistor-type viscosity sensor at the source-drain bias of 0.5 volts at room temperature versus the viscosity for various liquids in accordance with an embodiment of the present disclosure, where the fluctuation of the drain current can be calculated as the standard deviation of all the measurement points for respective fluids as shown in FIG. 4. Specifically, the viscosity of the fluid 2 can be determined by the processing unit 17 according to the electronic signal of the transistor-type viscosity sensor 10 measured by the electrical measurement unit 16 and based on the content of the look-up datum shown in FIG. 5A, FIG. 5B, and FIG. 5C.

In FIG. 5A, FIG. 5B, and FIG. 5C, the horizontal axis represents the viscosity of fluid in the unit of centipoise (cP), and the vertical axis represents the amount of the fluctuation of drain current measured in the unit of microampere. The Point P1 shows the amount of the fluctuation of drain current measured when the transistor-type viscosity sensor 10 is submerged in deionized water. The Point P2 shows the amount of the fluctuation of drain current measured when the transistor-type viscosity sensor 10 is submerged in dimethyl sulfoxide. The Point P3 shows the amount of the fluctuation of drain current measured when the transistor-type viscosity sensor 10 is submerged in ethanol.

The Point P4 shows the amount of the fluctuation of drain current measured when the transistor-type viscosity sensor 10 is submerged in air. The Point P5 shows the amount of the fluctuation of drain current measured when the transistor-type viscosity sensor 10 is submerged in glycerol. The Point P6 shows the amount of the fluctuation of drain current measured when the transistor-type viscosity sensor 10 is submerged in ethylene glycol. The Point P7 shows the amount of the fluctuation of drain current measured when the transistor-type viscosity sensor 10 is submerged in 1, 2-butandiol.

The following describes the operating principle of the transistor-type viscosity sensor 10, the viscosity measurement system 1 using the same, and the viscosity measuring method of the present disclosure. The viscosity of fluids is an index to the interaction and/or the force among the fluid molecules and therefore related to the motions of the fluid molecules at a certain temperature.

At room temperature, the low viscosity of the fluid indicates possible stronger molecular motions, leading to a more vigorous dipole change in local area, resulting in the larger fluctuation of the drain current. On the contrary, the high viscosity of the fluid indicates possible weaker molecular motions, leading to a smaller dipole change in local area, resulting in the smaller fluctuation of the drain current.

At room temperature, thermal energy is responsible for the molecular motions of fluids, which can be more described as the Brownian motions. The molecular motions of fluids will lead to the fluctuation of the surface dipole on the gate region 11G, eventually resulting in the fluctuation of the drain current of the semiconductor structure 11.

Please refer again to FIG. 4, the results show that the real time measurements of the drain current for the transistor-type viscosity sensor 10 in different fluids (such as glycerol, ethylene glycol, 1,2-butandiol, deionized water, dimethyl sulfoxide, and ethanol) are changed differently. In other words, the fluctuations of drain current of the semiconductor structure 11 in different fluids are different.

As shown in FIG. 4, fluids with different dipole moments induce different drain current for the semiconductor structure 11. Sticky fluids, such as ethylene glycol, 1,2-butandiol, and glycerol, with relative high viscosities, create relative small fluctuations, compared to those of fluent ones, such as water, ethanol, and dimethyl sulfoxide, which have low viscosities.

As mentioned above, the fluctuation of the drain current of the semiconductor structure 11 is resulted from the motions of the fluidic molecules, which cause the fluctuation of the surface dipole on the gate region 11G. Therefore, according to the relationship between the fluctuation of the drain current and the viscosity of the fluid, as shown in FIG. 4, it is practical to measure the viscosity of a fluid 2 with the transistor-type viscosity sensor 10 by monitoring the fluctuation of the drain current.

Please refer again to FIG. 5A, and FIG. 5B. A strong dependence of the current fluctuation to the viscosity can be observed. Fluids with relative higher viscosities have lower fluctuations in current. Fluids with relative lower viscosities have higher fluctuations in current. Moreover, the change in fluctuation per unit viscosity is larger in the low viscosity region than that of the high viscosity region.

It is worth noting that, there is one exception that is the fluctuation in air. The viscosity of the air is the smallest, but the fluctuation of the drain current in air is also the smallest. As considering the major composition of the air, which includes nitrogen ($N_2$), oxygen ($O_2$), and carbon dioxide ($CO_2$), the dipole moment of the air can be regarded as zero, due to no permanent dipole moment for these gases. The very tiny fluctuation of the drain current observed in air, which has the smallest viscosity, is due to the zero dipole moment of the air. Therefore, in a preferred embodiment, the fluid 2 has a dipole moment, which is more than zero debye. Or, in an alternative embodiment the fluid 2 has a dipole moment, which is more than 1 debye. In the instant disclosure, the fluid 2 has a dipole moment, which ranges from 1 to 5 debyes.

Figure 6:
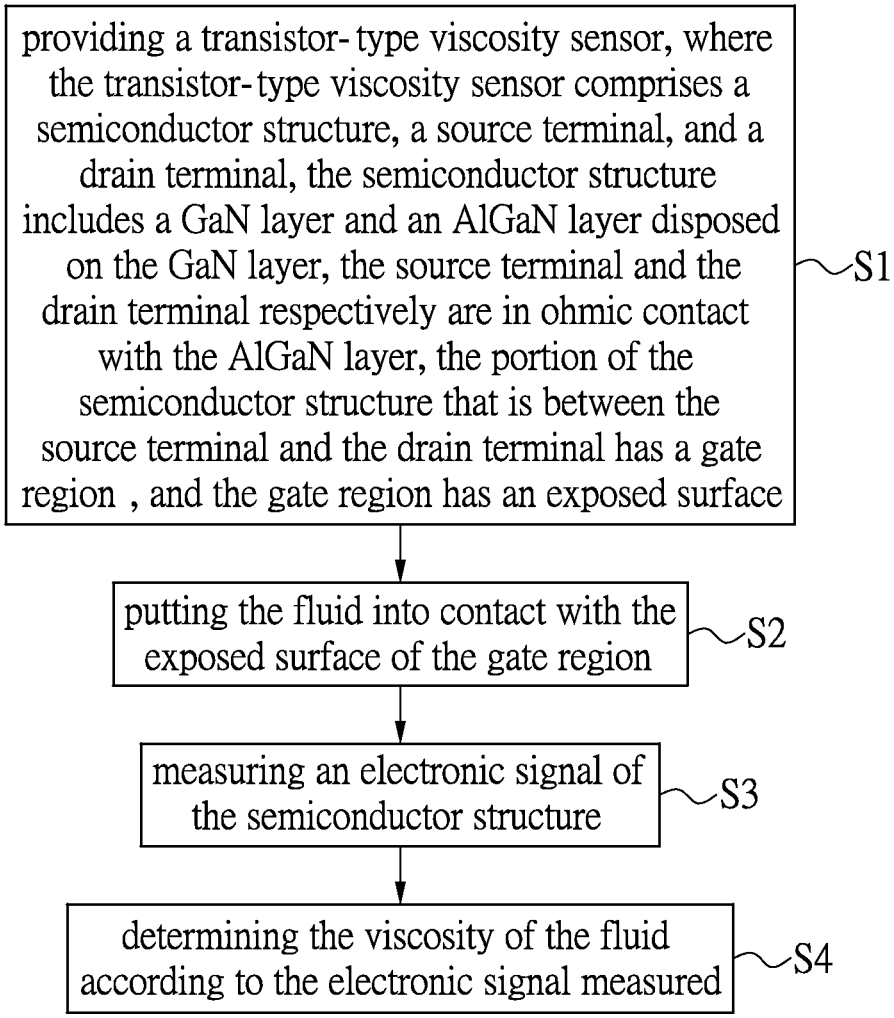
FIG. 6 illustrates a flowchart of a viscosity measuring method according to an embodiment of the present disclosure.

In accordance with the instant embodiment, the present disclosure also provides a viscosity measuring method, which is for measuring the viscosity of a fluid. Please refer to FIG. 6, which illustrates a flowchart of a viscosity measuring method according to an embodiment of the present disclosure. The viscosity measuring method comprising the steps of: firstly, providing a transistor-type viscosity sensor, where the transistor-type viscosity sensor comprises a semiconductor structure, a source terminal, and a drain terminal, the semiconductor structure includes a GaN layer and an AlGaN layer disposed on the GaN layer, the source terminal and the drain terminal respectively are in ohmic contact with the AlGaN layer, the portion of the semiconductor structure that is between the source terminal and the drain terminal has a gate region, and the gate region has an exposed surface (Step S1); then, putting the fluid into contact with the exposed surface of the gate region (Step S2); next, measuring an electronic signal of the semiconductor structure (Step S3); then, determining the viscosity of the fluid according to the electronic signal measured (Step S4).

In an exemplary embodiment, the above mentioned step of measuring electronic signal of the semiconductor structure may comprise measuring a current fluctuation of the semiconductor structure at a determined drain-source bias; and the above mentioned step of determining the viscosity of the fluid may comprise determining the viscosity of the fluid according to the current fluctuation measured by the electrical measurement unit.

Specifically, the above mentioned step of determining the viscosity of the fluid may comprise determining the viscosity of the fluid based on a look-up datum, where the content of the look-up datum includes the relationship between the viscosity of the fluid and the current fluctuation of the semiconductor structure.

In an alternatively embodiment, the above mentioned step of putting the fluid into contact with the exposed surface may comprise submerging the transistor-type viscosity sensor in the fluid, or dropping a portion of the fluid on the exposed surface of the gate region. The portion of the fluid that is dropped on the exposed surface can, as a specific example, have a volume of 1 to 10 microliters.

In accordance with the instant embodiment, the present disclosure also provides a transistor-type viscosity sensor 10, which is for measuring the viscosity of a fluid 2. The transistor-type viscosity sensor 10 comprises a semiconductor structure 11, a source terminal 12, and a drain terminal 13. The semiconductor structure 11 includes a GaN layer 112 and an AlGaN layer 113 disposed on the GaN layer 112. The source terminal 12 and the drain terminal 13 are in ohmic contact with the AlGaN layer 113. The portion of the semiconductor structure 11 that is between the source terminal 12 and the drain terminal 13 has a gate region 11G, which has an exposed surface 11S for being in contact with the fluid 2. When the exposed surface 11S of the gate region 11G is in contact with the fluid 2, a fluctuation of the current that is flowing in the semiconductor structure 11 is generated.

In accordance with the instant embodiment, the present disclosure provides a viscosity measurement system 1 and a viscosity measuring method, which utilize the semiconductor structure 11, including a GaN layer 112 and an AlGaN layer 113, serving as a high electron mobility transistor, and utilize the gate region 11G open to the fluid 2 to be measured, serving as the contact window for sensing, to allow the fluid 2 to cross the exposed surface 11S of the gate region 11G. Thus, the fluctuation of the surface dipole on the gate region 11G resulted from the motions of the molecules of the fluid 2 is sensed, whereby the viscosity of the fluid 2 can be determined by measuring electronic signal of the semiconductor structure 11.

In addition, through the viscosity measurement system 1 and/or the viscosity measuring method in accordance with instant disclosure, the viscosity of the fluid 2 which has a volume of only microliters can still be measured. Thus, the present viscosity measurement system and the viscosity measuring method can be variously applied, even in biochemistry or biomedical field, where it is only allowed to acquire a tiny amount of the fluid to be measured.

Since the GaN layer 112 and the AlGaN layer 113 are chemically stable, the present viscosity measurement system and the viscosity measuring method can be widely used in harsh environments (such as in acidic liquids, in alkaline liquids, at or high temperatures). Thus, the present viscosity measurement system and the viscosity measuring method can be suitable for measuring the viscosity of acidic liquid or alkaline liquid.

While the invention has been disclosed with respect to a limited number of embodiments, numerous modifications and variations will be appreciated by those skilled in the art. It is intended, therefore, that the following claims cover all such modifications and variations that may fall within the true spirit and scope of the invention.

What is claimed is:

1. A viscosity measurement system, for measuring the viscosity of a fluid with a dipole moment, the viscosity measurement system comprising:
   a transistor-type viscosity sensor, comprising:
      a semiconductor structure, comprising a GaN layer and an AlGaN layer disposed on the GaN layer;
      a source terminal, in ohmic contact with the AlGaN layer;
      a drain terminal, in ohmic contact with the AlGaN layer; and
      wherein the portion of the semiconductor structure that is between the source terminal and the drain terminal has a gate region, the gate region having an exposed surface for being in contact with the fluid with the dipole moment;
   an electrical measurement unit, in electrical connection with the source terminal and the drain terminal, for measuring an electronic signal of the semiconductor structure; and
   a processing unit, coupled to the electrical measurement unit, for determining the viscosity of the fluid with the dipole moment according to the electronic signal measured by the electrical measurement unit.

2. The viscosity measurement system of claim 1, wherein the electrical measurement unit is for measuring a current fluctuation of the semiconductor structure at a determined drain-source bias, and the processing unit is for determining the viscosity of the fluid according to the current fluctuation measured by the electrical measurement unit.

3. The viscosity measurement system of claim 2, wherein the processing unit includes a data storage module for storing a look-up datum, the content of which includes the relationship between the viscosity of the fluid and the current fluctuation of the semiconductor structure, and the processing unit is for determining the viscosity of the fluid based on the look-up datum.

4. The viscosity measurement system of claim 1, wherein the fluid has a dipole moment, which ranges from 1 to 5 debyes.

5. The viscosity measurement system of claim 1, wherein the exposed surface of the gate region has a width of 27 to 33 micrometers.

6. The viscosity measurement system of claim 1, wherein the mole percentage of Al of the AlGaN layer is 22% to 28%, and the thickness of the AlGaN layer is 13.5 to 16.5 nanometers.

7. The viscosity measurement system of claim 1, wherein the semiconductor structure is formed of an epitaxy wafer structure.

8. The viscosity measurement system of claim 1, wherein the semiconductor structure further comprises a substrate, and the GaN layer is disposed on the substrate.

9. The viscosity measurement system of claim 1, wherein the semiconductor structure further comprises a gold layer disposed on the portion of the AlGaN layer that comprises the gate region.

10. The viscosity measurement system of claim 1, wherein the semiconductor structure further comprises a passivation layer covering at least the source terminal and the drain terminal and exposing the exposed surface of the gate region.

11. A transistor-type viscosity sensor, for measuring the viscosity of a fluid with a dipole moment, the transistor-type viscosity sensor comprising:
 a semiconductor structure, comprising a GaN layer and an AlGaN layer disposed on the GaN layer;
 a source terminal, in ohmic contact with the AlGaN layer; and
 a drain terminal, in ohmic contact with the AlGaN layer;
 wherein the portion of the semiconductor structure that is between the source terminal and the drain terminal has a gate region, the gate region having an exposed surface for being in contact with the fluid with the dipole moment;
 wherein when the exposed surface of the gate region is in contact with the fluid with the dipole moment, a fluctuation of the current that is flowing in the semiconductor structure is generated by the molecular motions of the fluid with the dipole moment.

12. The transistor-type viscosity sensor of claim 11, wherein the fluid has a dipole moment, which ranges from 1 to 5 debyes.

13. The transistor-type viscosity sensor of claim 11, wherein the exposed surface of the gate region has a width of 27 to 33 micrometers.

14. The transistor-type viscosity sensor of claim 11, wherein the mole percentage of Al of the AlGaN layer is 22% to 28%, and the thickness of the AlGaN layer is 13.5 to 16.5 nanometers.

15. The transistor-type viscosity sensor of claim 11, wherein the semiconductor structure is formed of an epitaxy wafer structure.

16. The transistor-type viscosity sensor of claim 11, wherein the semiconductor structure further comprises a substrate, and the GaN layer is disposed on the substrate.

17. The transistor-type viscosity sensor of claim 11, wherein the semiconductor structure further comprises a gold layer disposed on the portion of the AlGaN layer that comprises the gate region.

18. The transistor-type viscosity sensor of claim 11, wherein the semiconductor structure further comprises a passivation layer covering at least the source terminal and the drain terminal and exposing the exposed surface of the gate region.

19. A viscosity measuring method, for measuring the viscosity of a fluid with a dipole moment, the viscosity measuring method comprising the steps of:
 providing a transistor-type viscosity sensor,
  wherein the transistor-type viscosity sensor comprises a semiconductor structure, a source terminal, and a drain terminal, the semiconductor structure includes a GaN layer and an AlGaN layer disposed on the GaN layer, the source terminal and the drain terminal respectively are in ohmic contact with the AlGaN layer, the portion of the semiconductor structure that is between the source terminal and the drain terminal has a gate region, and the gate region has an exposed surface;
 putting the fluid with the dipole moment into contact with the exposed surface of the gate region;
 measuring an electronic signal of the semiconductor structure; and
 determining the viscosity of the fluid with the dipole moment according to the electronic signal measured.

20. The viscosity measuring method of claim 19,
 wherein the measuring electronic signal of the semiconductor structure comprises:
  measuring a current fluctuation of the semiconductor structure at a determined drain-source bias; and
 wherein the determining the viscosity of the fluid comprises:
  determining the viscosity of the fluid according to the current fluctuation measured.

21. The viscosity measuring method of claim 20, wherein the determining the viscosity of the fluid comprises: determining the viscosity of the fluid based on a look-up datum, the content of which includes the relationship between the viscosity of the fluid and the current fluctuation of the semiconductor structure.

22. The viscosity measuring method of claim 19, wherein the putting the fluid into contact with the exposed surface comprises: submerging the transistor-type viscosity sensor in the fluid.

23. The viscosity measuring method of claim 19, wherein the putting the fluid into contact with the exposed surface comprises: dropping a portion of the fluid on the exposed surface of the gate region.

24. The viscosity measuring method of claim 23, wherein the portion of the fluid that is dropped on the exposed surface has a volume of 1 to 10 microliters.

25. The viscosity measuring method of claim 19, wherein the fluid has a dipole moment which ranges from 1 to 5 debyes.

26. The viscosity measuring method of claim 19, wherein the exposed surface of the gate region has a width of 27 to 33 micrometers.

27. The viscosity measuring method of claim 19, wherein the mole percentage of Al of the AlGaN layer is 22% to 28%, and the thickness of the AlGaN layer is 13.5 to 16.5 nanometers.

28. The viscosity measuring method of claim 19, wherein the semiconductor structure is formed of an epitaxy wafer structure.

29. The viscosity measuring method of claim 19, wherein the semiconductor structure further comprises a gold layer disposed on the portion of the AlGaN layer that comprises the gate region.

30. The viscosity measuring method of claim 19, wherein the semiconductor structure further comprises a passivation layer covering at least the source terminal and the drain terminal and exposing the exposed surface of the gate region.

* * * * *